(12) United States Patent
Anderson et al.

(10) Patent No.: US 8,118,844 B2
(45) Date of Patent: Feb. 21, 2012

(54) EXPANDABLE DEVICE FOR INSERTION BETWEEN ANATOMICAL STRUCTURES AND A PROCEDURE UTILIZING SAME

(75) Inventors: Kent M. Anderson, Memphis, TN (US); Eric C. Lange, Collierville, TN (US); Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 248 days.

(21) Appl. No.: 11/409,641

(22) Filed: Apr. 24, 2006

(65) Prior Publication Data

US 2007/0250060 A1    Oct. 25, 2007

(51) Int. Cl.
*A61B 17/88* (2006.01)
(52) U.S. Cl. .................. 606/279; 606/248; 606/249
(58) Field of Classification Search .............. 623/17.12, 623/17.16, 17.11, 17.13, 17.14, 17.15; 606/61, 606/246, 248, 249, 279, 192; 604/103.03, 604/103.05
See application file for complete search history.

(56) References Cited

U.S. PATENT DOCUMENTS

| | | | |
|---|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,053,257 A * | 9/1962 | Birtwell ................. 604/97.01 |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 3,860,969 A | 1/1975 | Arion |
| 3,867,728 A | 2/1975 | Stubstad et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |

(Continued)

FOREIGN PATENT DOCUMENTS

DE          2821678 A1       11/1979

(Continued)

OTHER PUBLICATIONS

English Translation of Taylor et al FR2816197, originally published May 10, 2005.*

(Continued)

*Primary Examiner* — Eduardo C Robert
*Assistant Examiner* — Jan Christopher Merene (57) ABSTRACT

A surgical implantation procedure and device according to which an expandable member is inserted between anatomical structures, and is expanded into engagement with the structures. The expansion is terminated when the member is in engagement with the structures.

11 Claims, 8 Drawing Sheets

U.S. PATENT DOCUMENTS

| | | |
|---|---|---|
| 4,553,273 A | 11/1985 | Wu |
| 4,554,914 A | 11/1985 | Kapp et al. |
| 4,573,454 A | 3/1986 | Hoffman |
| 4,573,966 A | 3/1986 | Weikl et al. |
| 4,592,341 A | 6/1986 | Omagari et al. |
| 4,599,086 A | 7/1986 | Doty |
| 4,604,995 A | 8/1986 | Stephens et al. |
| 4,610,662 A | 9/1986 | Weikl et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 4,969,888 A | 11/1990 | Scholten et al. |
| 5,000,166 A | 3/1991 | Karpf |
| 5,011,484 A | 4/1991 | Breard |
| 5,019,042 A | 5/1991 | Sahota |
| 5,035,712 A | 7/1991 | Hoffman |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,112,306 A | 5/1992 | Burton et al. |
| 5,171,278 A | 12/1992 | Pisharodi |
| 5,171,280 A | 12/1992 | Baumgartner |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,330,429 A | 7/1994 | Noguchi et al. |
| 5,342,305 A | 8/1994 | Shonk |
| 5,356,423 A | 10/1994 | Tihon et al. |
| 5,358,487 A | 10/1994 | Miller |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,403,341 A * | 4/1995 | Solar ............................ 606/198 |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,460,610 A | 10/1995 | Don Michael |
| 5,480,442 A | 1/1996 | Bertagnoli |
| 5,496,318 A | 3/1996 | Howland et al. |
| 5,518,498 A | 5/1996 | Lindenberg et al. |
| 5,540,689 A | 7/1996 | Sanders et al. |
| 5,549,679 A | 8/1996 | Kuslich |
| 5,554,191 A | 9/1996 | Lahille et al. |
| 5,562,662 A | 10/1996 | Brumfield et al. |
| 5,562,735 A | 10/1996 | Margulies |
| 5,562,736 A | 10/1996 | Ray et al. |
| 5,571,189 A * | 11/1996 | Kuslich ...................... 623/17.12 |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,597 A | 7/1997 | Krapiva |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,391 A | 12/1997 | Lin |
| 5,702,395 A | 12/1997 | Hopf |
| 5,702,452 A | 12/1997 | Argenson et al. |
| 5,702,454 A | 12/1997 | Baumgartner |
| 5,702,455 A | 12/1997 | Saggar |
| 5,707,390 A | 1/1998 | Bonutti |
| 5,716,416 A | 2/1998 | Lin |
| 5,720,762 A * | 2/1998 | Bass ............................ 606/192 |
| 5,723,013 A | 3/1998 | Jeanson et al. |
| 5,725,341 A | 3/1998 | Hofmeister |
| 5,746,762 A | 5/1998 | Bass |
| 5,749,916 A | 5/1998 | Richelsoph |
| 5,755,797 A | 5/1998 | Baumgartner |
| 5,800,547 A | 9/1998 | Schafer et al. |
| 5,800,549 A | 9/1998 | Bao et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,964,730 A | 10/1999 | Williams et al. |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,059,829 A | 5/2000 | Schlapfer et al. |
| 6,066,154 A | 5/2000 | Reiley et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,113,638 A | 9/2000 | Williams et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,143,031 A | 11/2000 | Knothe et al. |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,224,631 B1 | 5/2001 | Kohrs |
| 6,245,107 B1 | 6/2001 | Ferree |
| 6,293,949 B1 | 9/2001 | Justis et al. |
| 6,325,827 B1 | 12/2001 | Lin |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,383,221 B1 | 5/2002 | Scarborough et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 * | 7/2002 | Ferree ........................ 623/17.12 |
| 6,432,130 B1 * | 8/2002 | Hanson ........................ 623/1.11 |
| 6,436,140 B1 | 8/2002 | Liu et al. |
| 6,440,169 B1 | 8/2002 | Elberg et al. |
| 6,447,513 B1 | 9/2002 | Griggs |
| 6,447,546 B1 | 9/2002 | Bramlet et al. |
| 6,451,019 B1 | 9/2002 | Zucherman et al. |
| 6,500,178 B2 | 12/2002 | Zucherman et al. |

| | | |
|---|---|---|
| 6,511,508 B1 | 1/2003 | Shahinpoor et al. |
| 6,514,256 B2 | 2/2003 | Zucherman et al. |
| 6,520,991 B2 | 2/2003 | Huene |
| 6,527,803 B1 | 3/2003 | Crozet et al. |
| 6,554,833 B2 | 4/2003 | Levy et al. |
| 6,582,433 B2 | 6/2003 | Yun |
| 6,582,467 B1 | 6/2003 | Teitelbaum et al. |
| 6,592,585 B2 | 7/2003 | Lee et al. |
| 6,610,069 B2 | 8/2003 | Euteneuer et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,533 B1 | 5/2004 | Lozier |
| 6,733,534 B2 * | 5/2004 | Sherman .................. 623/17.16 |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,899,719 B2 * | 5/2005 | Reiley et al. .................. 606/192 |
| 6,902,580 B2 | 6/2005 | Fallin et al. |
| 6,905,512 B2 | 6/2005 | Paes et al. |
| 6,936,070 B1 * | 8/2005 | Muhanna .................. 623/17.12 |
| 6,946,000 B2 | 9/2005 | Senegas et al. |
| 6,958,077 B2 | 10/2005 | Suddaby |
| 6,969,404 B2 | 11/2005 | Ferree |
| 6,981,975 B2 | 1/2006 | Michelson |
| 6,981,981 B2 * | 1/2006 | Reiley et al. .................. 606/192 |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,201,772 B2 * | 4/2007 | Schwammenthal et al. . 623/2.18 |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,442,210 B2 | 10/2008 | Segal et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,666,205 B2 | 2/2010 | Weikel et al. |
| 7,749,252 B2 | 7/2010 | Zucherman et al. |
| 7,771,456 B2 | 8/2010 | Hartman et al. |
| 7,824,431 B2 | 11/2010 | McCormack |
| 7,862,615 B2 | 1/2011 | Carli et al. |
| 7,901,430 B2 | 3/2011 | Matsuura et al. |
| 7,927,354 B2 | 4/2011 | Edidin et al. |
| 7,942,847 B2 | 5/2011 | Stupecky et al. |
| 7,963,975 B2 * | 6/2011 | Criscuolo .................. 606/190 |
| 2001/0016743 A1 | 8/2001 | Zucherman |
| 2001/0049527 A1 | 12/2001 | Cragg |
| 2001/0049531 A1 * | 12/2001 | Reiley et al. .................. 606/93 |
| 2002/0082600 A1 | 6/2002 | Shaolian et al. |
| 2002/0143331 A1 | 10/2002 | Zucherman et al. |
| 2002/0177866 A1 | 11/2002 | Weikel et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2003/0176925 A1 | 9/2003 | Paponneau |
| 2003/0195628 A1 * | 10/2003 | Bao et al. .................. 623/17.12 |
| 2003/0220649 A1 | 11/2003 | Bao et al. |
| 2004/0010312 A1 | 1/2004 | Enayati |
| 2004/0010316 A1 | 1/2004 | William et al. |
| 2004/0064094 A1 | 4/2004 | Freyman |
| 2004/0083002 A1 | 4/2004 | Belef et al. |
| 2004/0087947 A1 | 5/2004 | Lim et al. |
| 2004/0097927 A1 * | 5/2004 | Yeung et al. .................. 606/61 |
| 2004/0097931 A1 | 5/2004 | Mitchell |
| 2004/0106995 A1 | 6/2004 | Le Couedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0172029 A1 | 9/2004 | Lerch |
| 2004/0186576 A1 * | 9/2004 | Biscup et al. .................. 623/17.12 |
| 2004/0186577 A1 | 9/2004 | Ferree |
| 2004/0199255 A1 | 10/2004 | Mathieu et al. |
| 2004/0260239 A1 | 12/2004 | Kusleika |
| 2004/0260397 A1 | 12/2004 | Lambrecht et al. |
| 2005/0004592 A1 * | 1/2005 | Criscuolo .................. 606/190 |
| 2005/0010293 A1 | 1/2005 | Zucherman et al. |
| 2005/0015140 A1 | 1/2005 | deBeer |
| 2005/0027358 A1 | 2/2005 | Suddaby |
| 2005/0033434 A1 | 2/2005 | Berry |
| 2005/0049590 A1 | 3/2005 | Alleyne et al. |
| 2005/0049708 A1 | 3/2005 | Atkinson et al. |
| 2005/0055031 A1 | 3/2005 | Lim |
| 2005/0056292 A1 | 3/2005 | Cooper |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0047282 A1 | 3/2006 | Gordon |
| 2006/0064165 A1 | 3/2006 | Zucherman et al. |
| 2006/0084983 A1 * | 4/2006 | Kim .................. 606/61 |
| 2006/0084985 A1 * | 4/2006 | Kim .................. 606/61 |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 * | 6/2006 | Kim .................. 606/90 |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149136 A1 | 7/2006 | Seto et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |

| | | | | | | |
|---|---|---|---|---|---|---|
| 2006/0224241 A1 | 10/2006 | Butler et al. | | 2008/0195152 A1 | 8/2008 | Altarac et al. |
| 2006/0235387 A1 | 10/2006 | Peterman | | 2008/0208341 A1 | 8/2008 | McCormack et al. |
| 2006/0235532 A1 | 10/2006 | Meunier et al. | | 2008/0215094 A1 | 9/2008 | Taylor |
| 2006/0241601 A1 | 10/2006 | Trautwein et al. | | 2008/0221685 A9 | 9/2008 | Altarac et al. |
| 2006/0241613 A1 | 10/2006 | Bruneau et al. | | 2008/0234824 A1 | 9/2008 | Youssef et al. |
| 2006/0241643 A1 | 10/2006 | Lim et al. | | 2008/0243250 A1 | 10/2008 | Seifert et al. |
| 2006/0241757 A1 | 10/2006 | Anderson | | 2008/0262617 A1 | 10/2008 | Froehlich et al. |
| 2006/0247623 A1 | 11/2006 | Anderson et al. | | 2008/0281359 A1 | 11/2008 | Abdou |
| 2006/0247640 A1 | 11/2006 | Blackwell et al. | | 2008/0281360 A1 | 11/2008 | Vittur et al. |
| 2006/0264938 A1 | 11/2006 | Zucherman et al. | | 2008/0281361 A1 | 11/2008 | Vittur et al. |
| 2006/0271044 A1 | 11/2006 | Petrini et al. | | 2009/0062915 A1 | 3/2009 | Kohm et al. |
| 2006/0271049 A1 | 11/2006 | Zucherman et al. | | 2009/0099610 A1 | 4/2009 | Johnson et al. |
| 2006/0271061 A1 | 11/2006 | Beyar et al. | | 2009/0105766 A1 | 4/2009 | Thompson et al. |
| 2006/0282075 A1 | 12/2006 | Labrom et al. | | 2009/0105773 A1 | 4/2009 | Lange et al. |
| 2006/0282079 A1 | 12/2006 | Labrom et al. | | 2009/0234389 A1 | 9/2009 | Chuang et al. |
| 2006/0293662 A1 | 12/2006 | Boyer et al. | | 2009/0240283 A1 | 9/2009 | Carls et al. |
| 2006/0293663 A1 | 12/2006 | Walkenhorst et al. | | 2009/0264927 A1 | 10/2009 | Ginsberg et al. |
| 2007/0005064 A1 | 1/2007 | Anderson et al. | | 2009/0270918 A1 | 10/2009 | Attia et al. |
| 2007/0010813 A1 | 1/2007 | Zucherman et al. | | 2009/0292316 A1 | 11/2009 | Hess |
| 2007/0032790 A1 | 2/2007 | Aschmann et al. | | 2009/0326538 A1 | 12/2009 | Sennett et al. |
| 2007/0043362 A1 | 2/2007 | Malandain et al. | | 2010/0121379 A1 | 5/2010 | Edmond |
| 2007/0043363 A1 | 2/2007 | Malandain et al. | | 2010/0191241 A1 | 7/2010 | McCormack et al. |
| 2007/0049935 A1 | 3/2007 | Edidin et al. | | 2010/0204732 A1 | 8/2010 | Aschmann et al. |
| 2007/0055274 A1* | 3/2007 | Appenzeller et al. ............ 606/90 | | 2010/0211101 A1 | 8/2010 | Blackwell et al. |
| 2007/0073289 A1 | 3/2007 | Kwak et al. | | 2010/0318190 A1 | 12/2010 | Collins et al. |
| 2007/0100340 A1 | 5/2007 | Lange et al. | | 2011/0054531 A1 | 3/2011 | Lamborne et al. |
| 2007/0112330 A1 | 5/2007 | Palasis | | 2011/0166600 A1 | 7/2011 | Lamborne et al. |
| 2007/0123861 A1 | 5/2007 | Dewey et al. | | | | |
| 2007/0142915 A1 | 6/2007 | Altarac et al. | | | FOREIGN PATENT DOCUMENTS | |
| 2007/0151116 A1 | 7/2007 | Malandain | | DE | 3922044 A1 | 2/1991 |
| 2007/0162000 A1 | 7/2007 | Perkins | | DE | 4012622 C1 | 7/1991 |
| 2007/0162136 A1 | 7/2007 | O'Neil et al. | | EP | 0322334 B1 | 2/1992 |
| 2007/0167945 A1 | 7/2007 | Lange et al. | | EP | 0767636 B1 | 1/1999 |
| 2007/0173822 A1 | 7/2007 | Bruneau et al. | | EP | 1004276 A1 | 5/2000 |
| 2007/0173823 A1 | 7/2007 | Dewey et al. | | EP | 1011464 B1 | 6/2000 |
| 2007/0191833 A1 | 8/2007 | Bruneau et al. | | EP | 1138268 A1 | 10/2001 |
| 2007/0191834 A1 | 8/2007 | Bruneau et al. | | EP | 1148850 B1 | 10/2001 |
| 2007/0191837 A1 | 8/2007 | Trieu | | EP | 1148851 B1 | 10/2001 |
| 2007/0191838 A1 | 8/2007 | Bruneau et al. | | EP | 1302169 A1 | 4/2003 |
| 2007/0198091 A1 | 8/2007 | Boyer et al. | | EP | 1330987 A1 | 7/2003 |
| 2007/0225807 A1 | 9/2007 | Phan et al. | | EP | 1552797 A2 | 7/2005 |
| 2007/0225810 A1 | 9/2007 | Colleran et al. | | EP | 202006018978 U1 | 2/2007 |
| 2007/0233068 A1 | 10/2007 | Bruneau et al. | | EP | 1854433 A1 | 11/2007 |
| 2007/0233074 A1 | 10/2007 | Anderson et al. | | EP | 1905392 A1 | 4/2008 |
| 2007/0233076 A1 | 10/2007 | Trieu | | EP | 1982664 A1 | 10/2008 |
| 2007/0233081 A1 | 10/2007 | Pasquet et al. | | FR | 2623085 A1 | 5/1989 |
| 2007/0233084 A1 | 10/2007 | Betz et al. | | FR | 2625097 A1 | 6/1989 |
| 2007/0233089 A1 | 10/2007 | DiPoto et al. | | FR | 2681525 A1 | 3/1993 |
| 2007/0250060 A1 | 10/2007 | Anderson et al. | | FR | 2700941 A1 | 8/1994 |
| 2007/0270823 A1 | 11/2007 | Trieu et al. | | FR | 2703239 A1 | 10/1994 |
| 2007/0270824 A1 | 11/2007 | Lim et al. | | FR | 2707864 A1 | 1/1995 |
| 2007/0270825 A1 | 11/2007 | Carls et al. | | FR | 27117675 A1 | 9/1995 |
| 2007/0270826 A1 | 11/2007 | Trieu et al. | | FR | 2722087 A1 | 1/1996 |
| 2007/0270827 A1 | 11/2007 | Lim et al. | | FR | 2722088 A1 | 1/1996 |
| 2007/0270828 A1 | 11/2007 | Bruneau et al. | | FR | 2724554 A1 | 3/1996 |
| 2007/0270829 A1 | 11/2007 | Carls et al. | | FR | 2725892 A1 | 4/1996 |
| 2007/0270834 A1 | 11/2007 | Bruneau et al. | | FR | 2730156 A1 | 8/1996 |
| 2007/0270874 A1 | 11/2007 | Anderson | | FR | 2731643 A1 | 9/1996 |
| 2007/0272259 A1 | 11/2007 | Allard et al. | | FR | 2775183 A1 | 8/1999 |
| 2007/0276368 A1 | 11/2007 | Trieu et al. | | FR | 2799948 A1 | 4/2001 |
| 2007/0276369 A1 | 11/2007 | Allard et al. | | FR | 2816197 * | 5/2002 |
| 2007/0276493 A1 | 11/2007 | Malandain et al. | | FR | 2816197 A1 | 5/2002 |
| 2007/0276496 A1* | 11/2007 | Lange et al. ............ 623/17.12 | | JP | 02-224660 | 9/1990 |
| 2007/0276497 A1 | 11/2007 | Anderson | | JP | 09-075381 | 3/1997 |
| 2007/0282443 A1 | 12/2007 | Globerman et al. | | JP | 2003079649 | 3/2003 |
| 2008/0021457 A1 | 1/2008 | Anderson et al. | | SU | 988281 | 1/1983 |
| 2008/0021460 A1 | 1/2008 | Bruneau et al. | | SU | 1484348 A1 | 6/1989 |
| 2008/0058934 A1 | 3/2008 | Malandain et al. | | SU | 1484348 | 7/1989 |
| 2008/0097446 A1 | 4/2008 | Reiley et al. | | WO | WO 94/26192 | 11/1994 |
| 2008/0114357 A1 | 5/2008 | Allard et al. | | WO | WO 94/26195 | 11/1994 |
| 2008/0114358 A1 | 5/2008 | Anderson et al. | | WO | WO 97/18769 | 5/1997 |
| 2008/0114456 A1 | 5/2008 | Dewey et al. | | WO | WO 98/20939 | 5/1998 |
| 2008/0147190 A1 | 6/2008 | Dewey et al. | | WO | WO 99/26562 | 6/1999 |
| 2008/0161818 A1 | 7/2008 | Kloss et al. | | WO | WO 99/59669 | 11/1999 |
| 2008/0167685 A1 | 7/2008 | Allard et al. | | WO | WO 00/44319 | 8/2000 |
| 2008/0177306 A1 | 7/2008 | Lamborne et al. | | WO | WO 01/54598 A1 | 8/2001 |
| 2008/0183209 A1 | 7/2008 | Robinson et al. | | WO | WO 03/057055 A1 | 7/2003 |
| 2008/0183211 A1 | 7/2008 | Lamborne et al. | | WO | WO 2004/047689 A1 | 6/2004 |
| 2008/0183218 A1 | 7/2008 | Mueller et al. | | WO | WO 2004/047691 A1 | 6/2004 |

| | | |
|---|---|---|
| WO | 2004/084743 A1 | 10/2004 |
| WO | WO 2004/084768 A2 | 10/2004 |
| WO | 2004/110300 A2 | 12/2004 |
| WO | WO 2005/002466 * | 1/2005 |
| WO | WO 2005/002474 A1 | 1/2005 |
| WO | 2005/009300 | 2/2005 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO2006025815 | 3/2006 |
| WO | WO 2006/064356 A1 | 6/2006 |
| WO | WO 2007/034516 A1 | 3/2007 |
| WO | WO2007038349 | 4/2007 |
| WO | WO2007052975 | 5/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |
| WO | 2009/149079 A1 | 12/2009 |

OTHER PUBLICATIONS

U.S. Appl. No. 11/376,991, filed Mar. 16, 2006, Anderson, et al.
U.S. Appl. No. 11/359,070, filed Feb. 22, 2006, Bruneau. et al.
U.S. Appl. No. 11/333,919, filed Jan. 18, 2006, Dewey, et al.
U.S. Appl. No. 11/334,691, filed Jan. 18, 2006, Lange, et al.
U.S. Appl. No. 11/271,018, filed Nov. 10, 2005, Dewey, et al.
U.S. Appl. No. 11/261,386, filed Oct. 27, 2005, Lange, et al.
U.S. Appl. No. 11/167,775, filed Jun. 27, 2005, Anderson, et al.
U.S. Appl. No. 11/095,215, filed Mar. 31, 2005, Anderson.
U.S. Appl. No. 11/095,214, filed Mar. 31, 2005, Anderson.
European Patent Office, International Searching Authority,Notification of Transmittal of the International Search Report and the Written Opinion of the International Searching Authority or the Declaration, International Application No. PCT/US2007/073604, Dec. 17, 2007, 13 pages.
European Patent Office, International Searching Authority, Notification of Transmittal of the International Search Report and the Written Opinion of the International Searching Authority or the Declaration, International Application No. PCT/US2007/066051, Apr. 5, 2007, 13 pages.
European Patent Office, International Searching Authority, Notification of Transmittal of the International Search Report and the Written Opinion of the International Searching Authority or the Declaration, International Application No. PCT/US2007/062405, Aug. 2, 2007, 9 pages.
"Dispositivo Intervertebrale Ammortizzante DIAM," date unknown, p. 1.
"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," SPINE, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Duff, "Methyl Methacrylate in Spinal Stabilization," Techniques in Spinal Fusion and Stabilization, Hitchon et al., eds., 1995, pp. 147-151, Ch. 14, Thieme, New York.
Ebara et al., "Inoperative Measurement of Lumbar Spinal Instability," SPINE, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. 5186-5191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," SPINE, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
Mcdonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Impianto Posteriore Ammortizzante," S.O.T.I.M.I. Societè di Ortopedia e Traumatologia dell'Italia Meridionale e Insulare 90 ° Congresso, Jun. 21-23, 2001, Paestum.
Petrini et al., "Stabilizzazione Elastica," Patologia Degenerative del Rachide Lombare, Oct. 5-6, 2001, Rimini.
Porter, "Spinal Stenosis and Neurogenic Claudication," SPINE, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrate Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrate, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Discord Tech., 2006, vol. 00, No. 00, pp. 1-7.

Buric et al., "DIAM Device for Low Back Pain in Degenerative Disc Disease 24 Months Follow-up," Advances in Minimally Invasive Surgery And Therapy For Spine and Nerves, Alexandre et al., eds., 2011, pp. 177-182, Spinger-Verlat/Wien.

Phillips et al., "Biomechanics of Posterior Dynamic Stabiling Device (DIAM) After Facetectomy and Disectomy," the Spine Journal, 2006, vol. 6, pp. 714-722.

Taylor et al., "Device for Intervertebral Assisted Motion: Technique and Intial Results," 22 Neurosurg. Focus, Jan. 2007, vol. 22, No. 1, pp. 1-6.

Wilke et al., "Biomedical Effect of Different Lumbar Interspinous Implants on Flexibilty and Intradiscal Pressure," Eur Spine J., vol. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

* cited by examiner

EXPANDABLE DEVICE FOR INSERTION BETWEEN ANATOMICAL STRUCTURES AND A PROCEDURE UTILIZING SAME

BACKGROUND

The present invention relates to an expandable device for insertion between anatomical structures and a procedure utilizing same.

It is often desirable to insert a device between anatomical structures for several reasons. For example, it can be inserted between two structures in a manner so that it engages the structures and serves as an implant for stabilizing the structures and absorbing shock. Alternately, a device can be temporarily inserted between the structures and function to distract the structures to permit another device, such as a prosthesis, to be implanted between the structures. According to another example, a device can be inserted between the structures and distract the structures to permit another surgical procedure to be performed in the space formed by the distraction, after which the device is released and removed.

Although devices have been designed for one or more of the above uses, they are not without problems. For example, it is often difficult to insert the device without requiring excessive invasion of the anatomy, damage to the adjacent anatomical structures, or over-distraction. Embodiments of the present invention improve upon these techniques and various embodiments of the invention may possess one or more of the above features and advantages, or provide one or more solutions to the above problems existing in the prior art.

DETAILED DESCRIPTION

Figure 1:
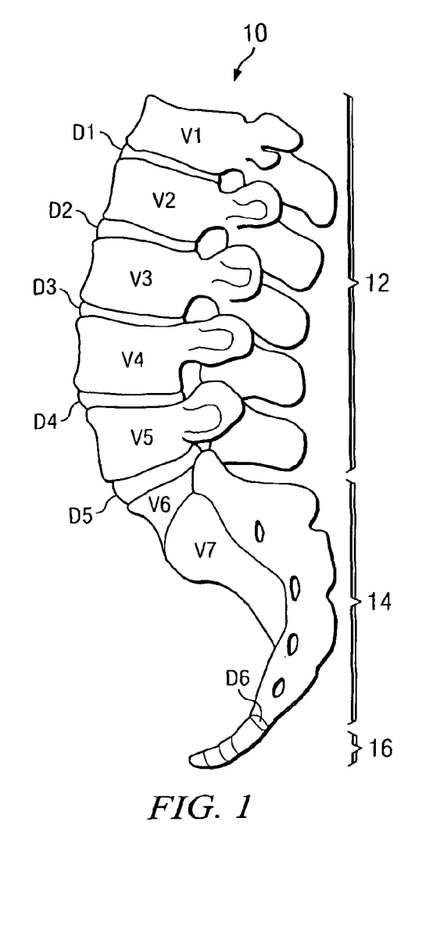
FIG. 1 is a side elevational view of an adult human vertebral column.
Figure 2:
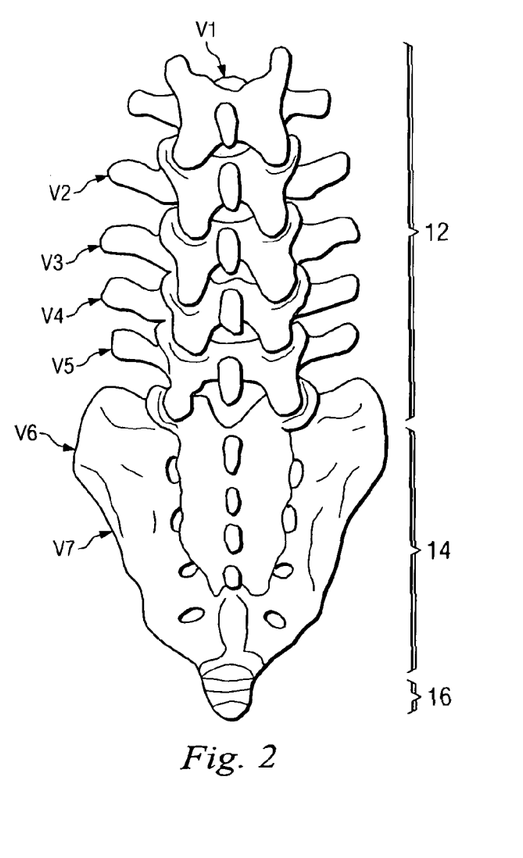
FIG. 2 is a posterior elevational view of the column of FIG. 1.

With reference to FIGS. 1 and 2, the reference numeral 10 refers, in general, to the lower portion of a human vertebral column. The column 10 includes a lumbar region 12, a sacrum 14, and a coccyx 16. The flexible, soft portion of the column 10, which includes the thoracic region and the cervical region, is not shown.

The lumbar region 12 of the vertebral column 10 includes five vertebrae V1, V2, V3, V4 and V5 separated by intervertebral discs D1, D2, D3, and D4, with the disc D1 extending between the vertebrae V1 and V2, the disc D2 extending between the vertebrae V2 and V3, the disc D3 extending between the vertebrae V3 and V4, and the disc D4 extending between the vertebrae V4 and V5.

The sacrum 14 includes five fused vertebrae, one of which is a superior vertebra V6 separated from the vertebra V5 by a disc D5. The other four fused vertebrae of the sacrum 14 are referred to collectively as V7. A disc D6 separates the sacrum 14 from the coccyx 16, which includes four fused vertebrae (not referenced).

Figure 3:
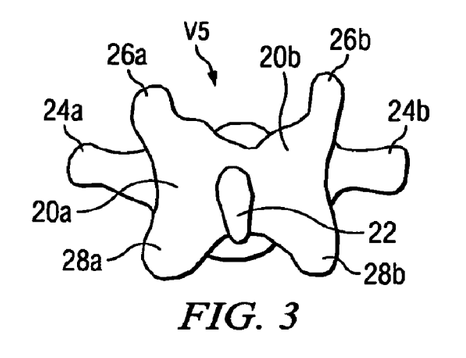
FIG. 3 is an elevational view of one of the vertebrae of the column of FIGS. 1 and 2.

With reference to FIG. 3, the vertebra V5 includes two laminae 20a and 20b extending to either side (as viewed in FIG. 2) of a spinous process 22 that extends posteriorly from the juncture of the two laminae. Two transverse processes 24a and 24b extend laterally from the laminae 20a and 20b, respectively. Two articular processes 26a and 26b extend superiorly from the laminae 20a and 20b, respectively, and two articular processes 28a and 28b extend inferiorly from the laminae 20a and 20b, respectively. The inferior articular processes 28a and 28b rest in the superior articular process of the vertebra V2 to form a facet joint. Since the vertebrae V1-V4 are similar to the vertebra V5, and since the vertebrae V6 and V7 are not involved in the present invention, they will not be described in detail.

It will be assumed that, for one or more of the reasons set forth above, the vertebrae V4 and V5 are not being adequately supported by the disc D4 and that it is therefore necessary to provide supplemental support and stabilization of these vertebrae. To this end, and referring to FIGS. 4A and 4B, device 30 according to an embodiment of the invention is provided and consists of a hollow expandable member 32 having a generally rectangular shape. The member 32 is fabricated from a relatively soft, inflatable material so that the member can be expanded and can function in the manner to be described.

One end of a tube 34 registers with an opening in the member 32 and the other end is connectable to a source (not shown) of fluid for inflating the member. The fluid could be air, water, a curable polymer, or any other suitable fluid. The member 32 is shown in a rolled-up, unexpanded state in FIG. 4A, with a pair of strings 36 extending around the member 32 to retain it in its rolled-up condition. To transform the member from its unexpanded, rolled-up, condition of FIG. 4A to its expanded condition of FIG. 4B, the strings 36 are removed and fluid is introduced into the member, via the tube 34.

Figure 4A:
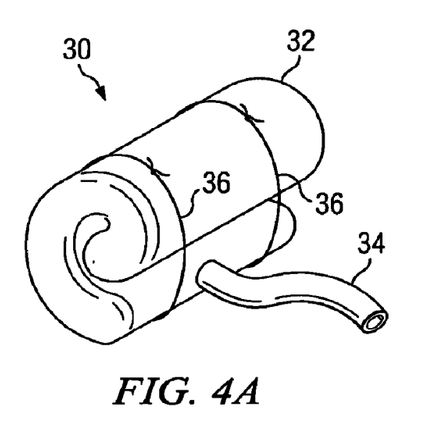
FIG. 4A is an isometric view of a device for implantation in the column of FIGS. 1-3.
Figure 4B:
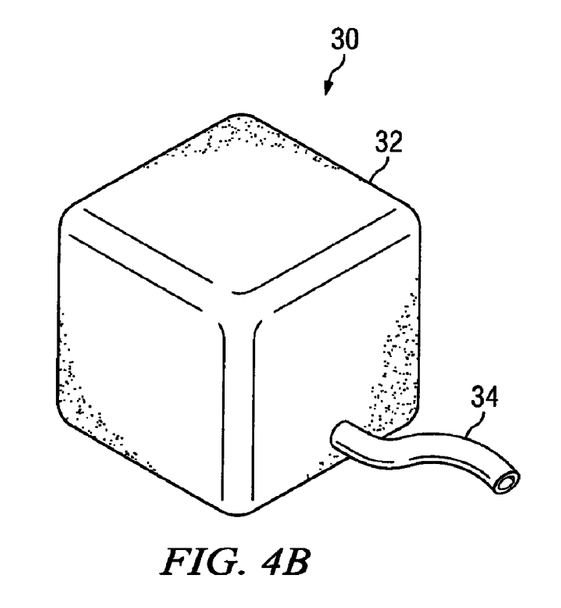
FIG. 4B is a view similar to that of FIG. 4A but depicting the device of FIG. 4A in an expanded condition.
Figure 5A:
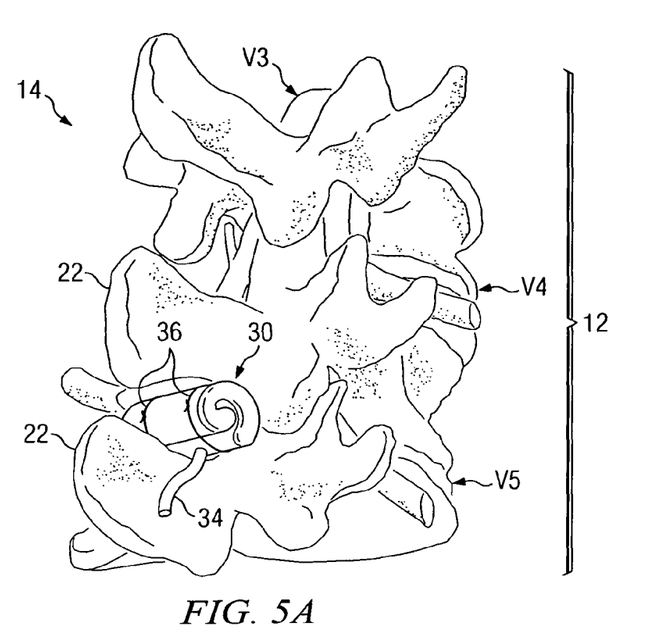
FIG. 5A is an enlarged, partial, isometric view of a portion of the column of FIGS. 1 and 2, including the lower three vertebrae of the column, with the device of FIG. 4A implanted between two adjacent vertebrae.

Referring to FIG. 5A, the device 30 is initially inserted between the processes 22 in its rolled-up, collapsed, or compressed, condition of FIG. 4A. In this position, the device 30 easily fits between the processes 22 in a relatively loose arrangement, i.e., the member is not pressed against the processes with any appreciable force.

Figure 5B:
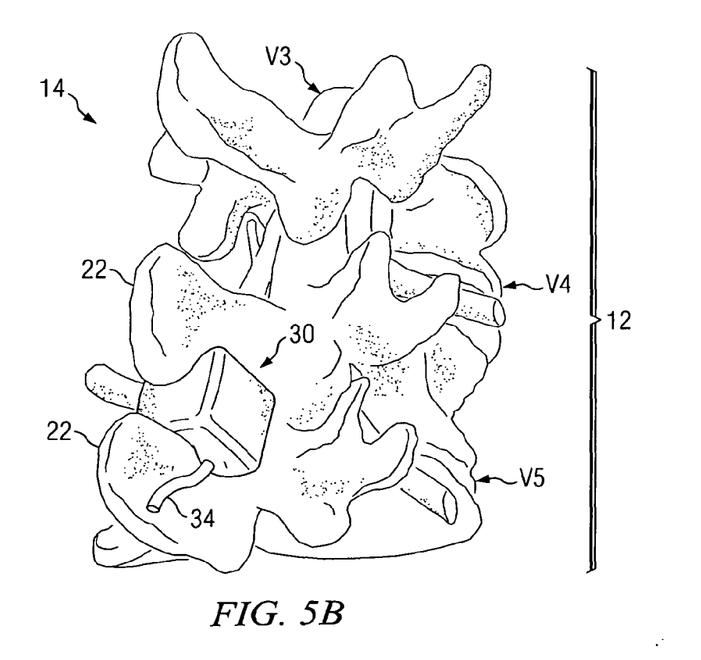
FIG. 5B is a view similar to that of FIG. 5A, but depicting the implanted device of FIG. 5A in its expanded condition of FIG. 4B.

The surgeon then removes the strings 36 from the rolled up member 32 and introduces fluid into the member, via the tube 34. This causes the member 32 to expand to its expanded condition of FIGS. 4B and 5B in which the corresponding outer surfaces of the member 32 press against the processes 22. When the resulting forces are sufficient to lock, or retain, the device 30 in the implanted position of FIG. 5B, the introduction of the fluid is terminated, and the device 30 is firmly implanted between the processes 22. Alternately, the strings 36 are not manually removed prior to the expansion of the member 32, but rather are made of a relatively weak, or fragile, material so that they will break in response to the forces thereon caused by the expansion of the member 32.

The presence of the device 30 prevents the collapse of the intervertebral space between the adjacent vertebrae and thus stabilizes the vertebral column 10. The flexible nature of the device 30 does not cause any damage to the processes 22 and absorbs shock that contributes to the dynamic stabilization of the vertebral column 10.

Figure 6A:
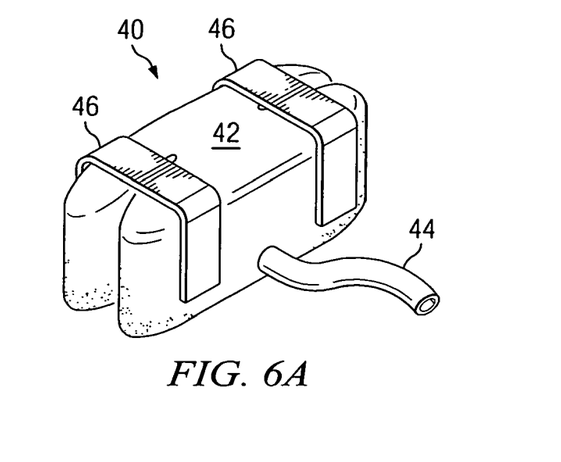
FIGS. 6A and 6B are views similar to those of FIGS. 4A and 4B, respectively, but depicting an alternate embodiment of a device for implantation in the column of FIGS. 1-3.
Figure 6B:
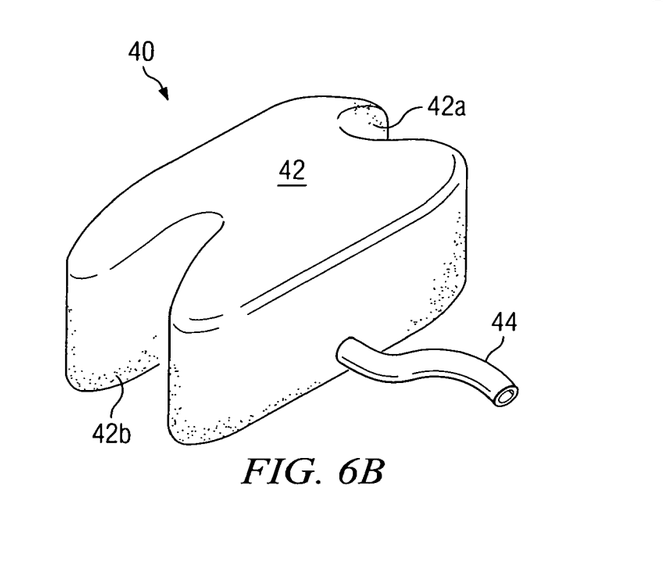

Referring to FIGS. 6A and 6B, a device 40 according to an embodiment of the invention is provided and consists of a hollow expandable member 42 having a generally rectangular shape with two large notches, or saddles, 42a and 42b formed at each end. The member 42 is fabricated from a relatively soft, inflatable material so that it can function in the manner to be described.

One end of a tube 44 registers with an opening in the member 42, and the other end of the tube is connectable to a source of fluid for inflating the member. The fluid could be air, water, a curable polymer, or any other suitable fluid.

The member 42 is shown in a collapsed, or compressed, condition in FIG. 6A, and it is maintained in this condition by a pair of spaced U-shaped retaining members, or clamps, 46 that extend over the upper surface of the body member, as viewed in FIG. 6A, and along two side walls thereof.

The device 40 is initially inserted between the processes 22 (FIG. 5A) with the body member 42 in the unexpanded, collapsed state of FIG. 6A. In this position, the device 40 easily fits between the processes 22 in a relatively loose arrangement, i.e., the device is not pressed against the processes with any appreciable force. The surgeon then removes the retaining members 46 from the member 42 and introduces fluid into the member, via the tube 44. This causes the member 42 to expand to its expanded condition of FIG. 6B in which the corresponding outer surfaces of the member 42 press against the processes 22.

When the resulting forces are sufficient to lock, or retain, the device 40 in the implanted position, the introduction of the fluid is terminated, and the device 40 is firmly implanted between the processes 22. Alternately, the retaining members 46 are not manually removed prior to the expansion of the member 42, but rather are made of a relatively weak, or fragile, material so that they will break in response to the forces thereon caused by the expansion of the member 42.

The presence of the implanted expanded device 40 prevents the collapse of the intervertebral space between the adjacent vertebrae and thus stabilizes the vertebral column 10. The soft nature of the material making up the body member 42 does not cause any damage to the processes 22 and absorbs shock, which contributes to the dynamic stabilization of the vertebral column.

Figure 7A:
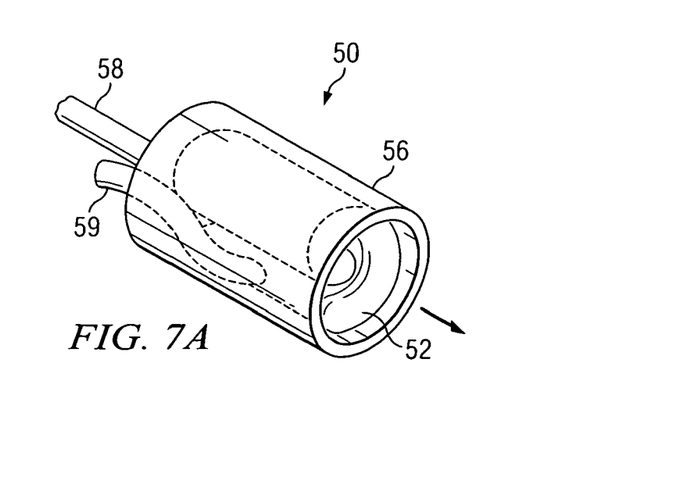
FIGS. 7A and 7B are views similar to those of FIGS. 4A and 4B, respectively, but depicting an alternate embodiment of a device for implantation in the column of FIGS. 1-3.

Referring to FIG. 7A, a device 50 according to an embodiment of the invention is provided and consists of a member 52 that is identical to the member 42 of the previous embodiment. One end of a tube 54 registers with an opening in the wall of the member 52, and the other end of the tube is connectable to a source of fluid for inflating the wall of the member 52 when it is removed from the sleeve 54. The fluid could be air, water, a curable polymer, or any other suitable fluid.

The member is shown in a folded, or collapsed, state in FIG. 7A and is contained in a hollow cylindrical retaining sleeve 54. The member 52 is fabricated from a relatively soft, inflatable material so that its wall can be expanded and so that the member can function in the manner to be described. The sleeve 56 maintains the member in its collapsed state. A push rod 58 is provided for pushing the member 52 out of the sleeve 56 under conditions to be described.

Figure 7B:
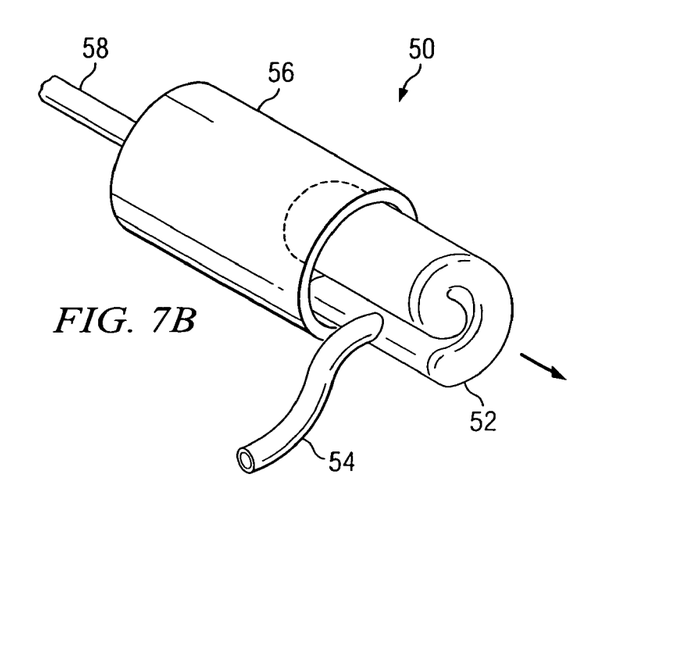
Figure 8A:
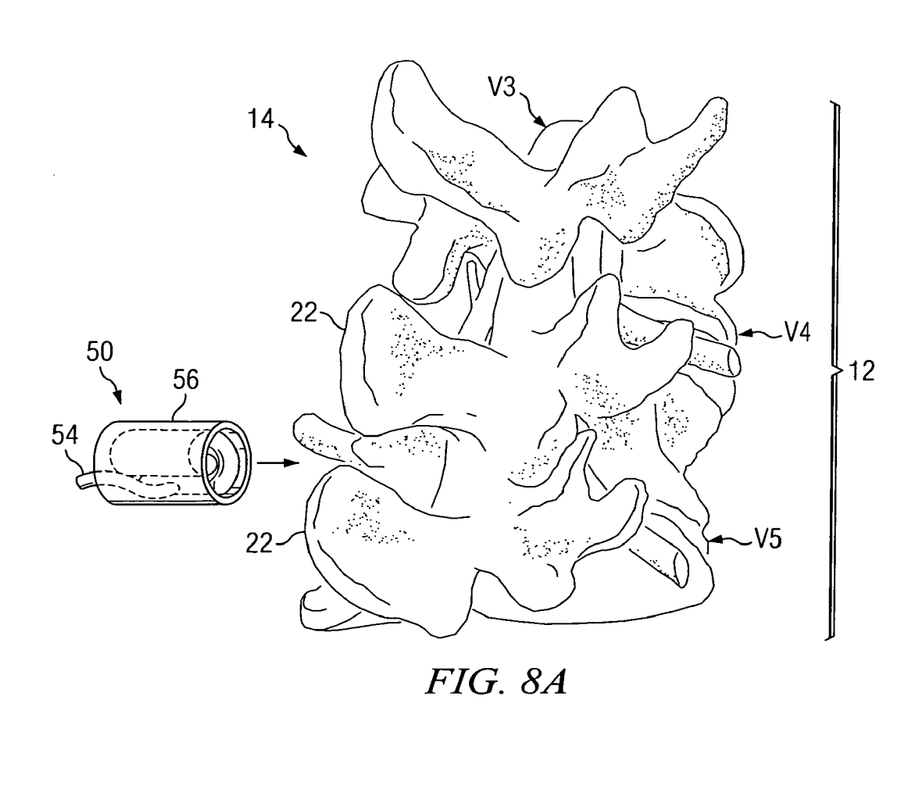
FIG. 8A-8C are enlarged, partial, isometric views of a portion of the column of FIGS. 1 and 2, including the lower three vertebrae of the column, depicting the procedure of inserting the device of FIGS. 7A and 7B between two adjacent vertebrae.
Figure 8B:
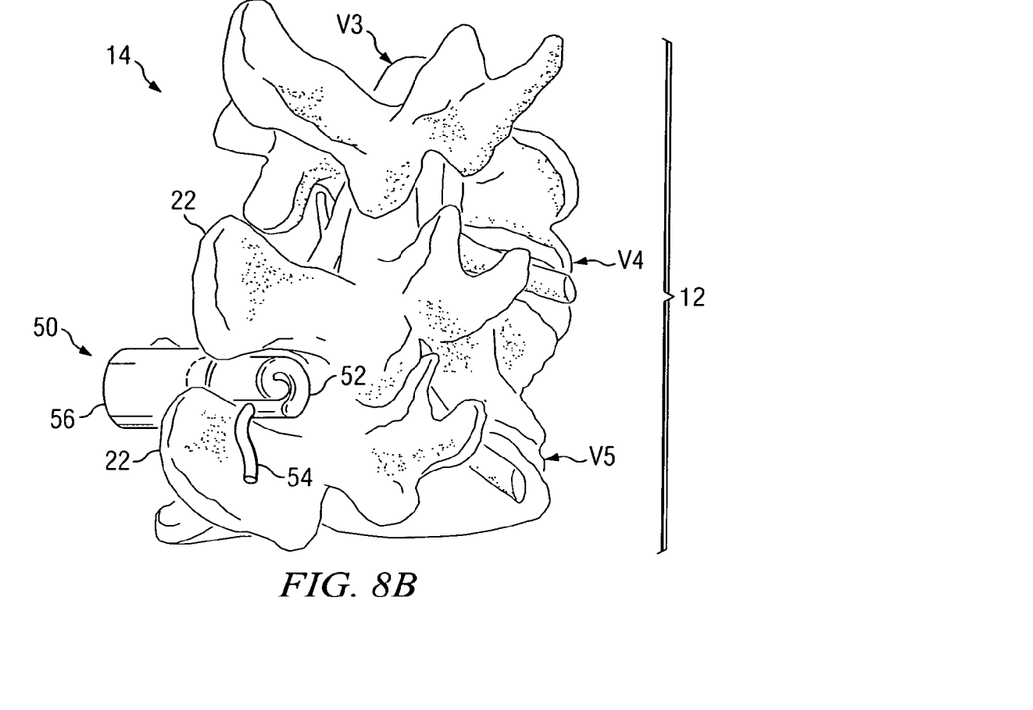
Figure 8C:
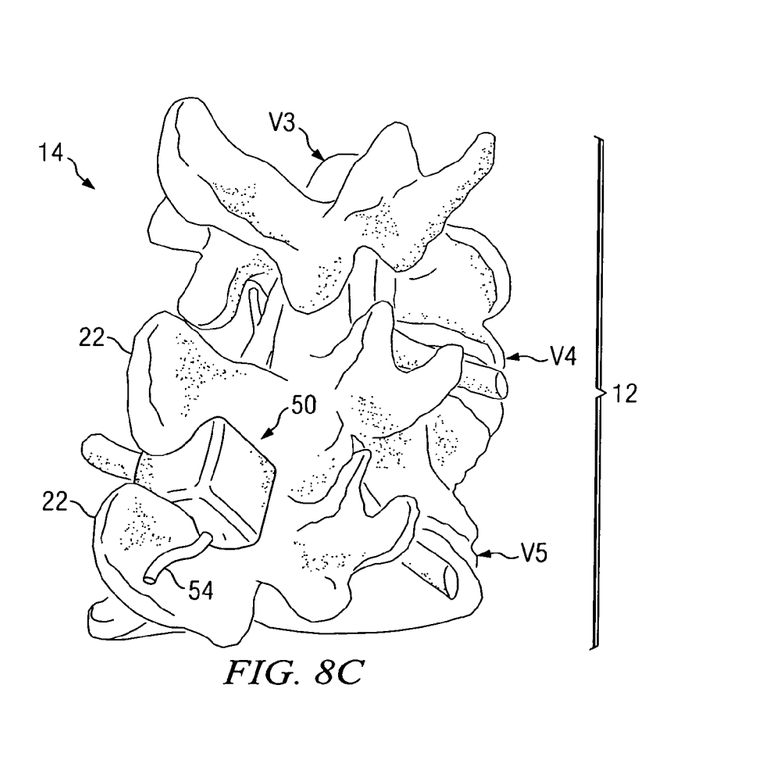

The device 50, with the folded member contained in the sleeve, is initially positioned adjacent the processes 22 as shown in FIG. 8A, and an axially-directed force is applied to the push rod 58 in the direction indicated by the arrow in FIG. 8A, to push the member 52 out of the sleeve 56 and towards the processes, as shown in FIGS. 7B and 8B. This pushing continues until the member 52 is pushed completely out of the sleeve 56, and into a position between the processes 22 in a relatively loose arrangement, i.e., the member is not pressed against the processes with any appreciable force. The surgeon then introduces fluid into the member 52, via the tube 54. This causes the member 52 to expand to its expanded condition shown in FIG. 8B in which the corresponding outer surfaces of the member press against the processes 22. When the resulting forces are sufficient to lock, or retain, the device 50 in the implanted position, the introduction of the fluid is terminated, and the device 50 is firmly implanted between the processes 22.

The presence of the implanted, expanded device 50 prevents the collapse of the intervertebral space between the adjacent vertebrae and thus stabilizes the vertebral column 10. The soft nature of the material making up the body member 52 does not cause any damage to the processes 22 and absorbs shock, which contributes to the dynamic stabilization of the vertebral column.

Figure 9A:
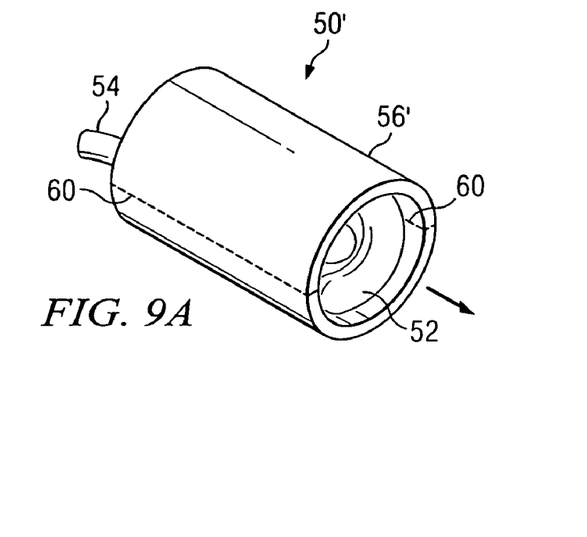
FIG. 9A is a view similar to those of FIGS. 4A, 6A, and 7A, but depicting an alternate embodiment of a device for implantation in the column of FIGS. 1-3.
Figure 9B:
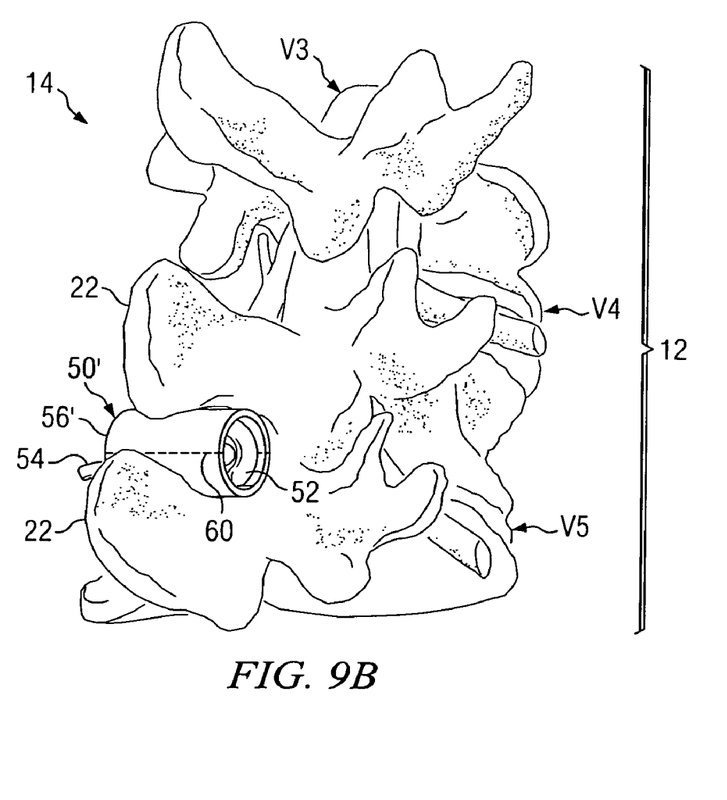
FIGS. 9B and 9C are views similar to those of FIGS. 5A and 5C, respectively, but depicting the insertion procedure for the device of FIG. 9A.
Figure 9C:
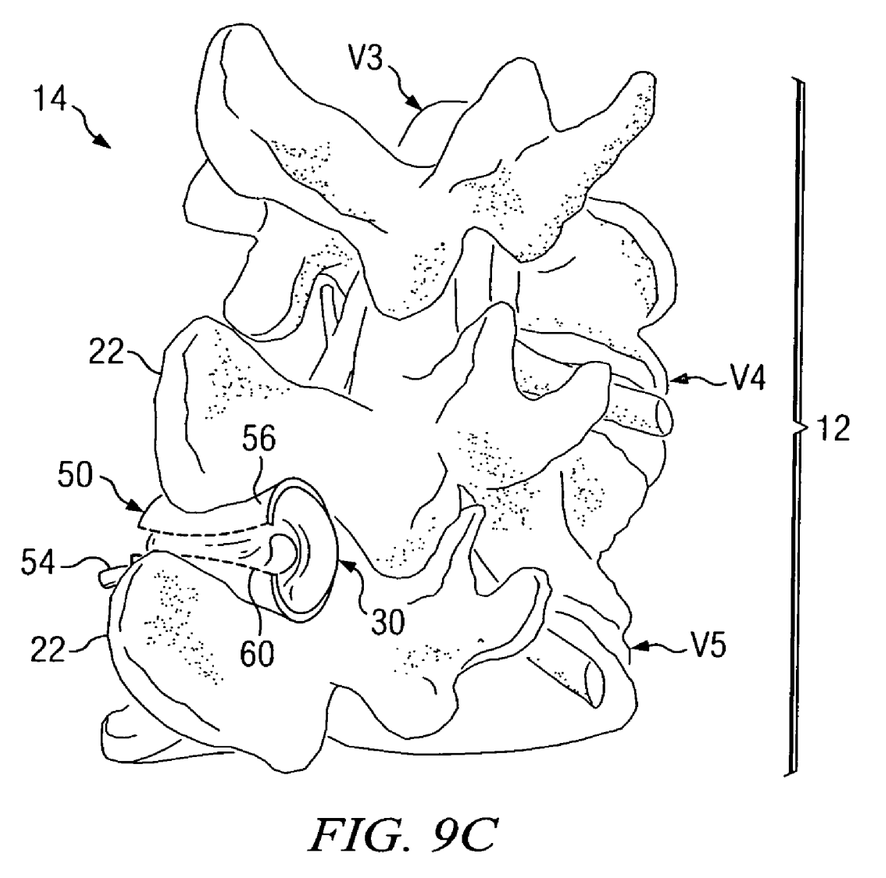

The embodiment of FIGS. 9A-9C is similar to that of the previous embodiment and identical components are given the same reference numerals. According to the embodiment of FIGS. 9A-9C, a device 50' is provided that is similar to the device 50 of the previous embodiment with the exceptions that the sleeve 56 of the previous embodiment is replaced by a sleeve 56', and the push rod 58 of the previous embodiment is eliminated. The sleeve 56' is similar to the sleeve 56 of the previous embodiment and, as such, contains the member 52, but has series of axially-extending perforations 60 provided in two diametrically-opposed portions of its wall. The perforations 60 are designed to allow the wall portions to break apart when the member 52 is expanded against the sleeve 56' under conditions to be described.

The device 50', with the folded member 52 contained in the sleeve 56' as shown in FIG. 9A, is inserted between the processes 22 in a relatively loose arrangement as shown in FIG. 9B. The surgeon then introduces fluid into the member 52, via the tube 54, which causes the member 52 to expand. During this expansion, the resultant forces acting on the sleeve 56' causes the sleeve to break-away, or tear, along the perforations 60 permitting the expanded member 52 to press against the processes 22, as shown in FIG. 9C. When the resulting forces are sufficient to lock, or retain, the device 50' in the implanted position, the introduction of the fluid is terminated, and the device 50' is firmly implanted between the processes 22.

The presence of the implanted, expanded device 50' prevents the collapse of the intervertebral space between the adjacent vertebrae and thus stabilizes the vertebral column 10. The soft nature of the material making up the body member 52 does not cause any damage to the processes 22 and absorbs shock, which contributes to the dynamic stabilization of the vertebral column.

It is understood that, in each of the above embodiments, after the strings 36, the retaining members 46, and the sleeves 56 and 56' have been removed from their respective body members 32, 42 and 52, they can be disposed of by the surgeon. Alternately, they can be fabricated from a resorbable, bio-absorbable, or dissolvable material that will not require disposal.

It is also understood that the term "expandable," as used herein, is meant to cover the situation in which the body members 32, 42 and 52 are initially folded, or wadded up, and then allowed to return to their normal state; or the situation in which the body members are actually inflated in response to the introduction of the fluid; or both.

It is further understood that, in each of the above embodiments, the devices 30, 40, 50 and 50 do not necessarily have to function as an implant as described in the example above, but rather can be used in other different procedures. For example, each device 30, 40, and 50 can be inserted between the structures, such as the processes used in the above examples, and expanded to an extent that it engages and distracts, or moves, the structures in a direction away from each other, to permit another device, such as a prosthesis, to be implanted between the structures or in an area near the structures. According to another example, each device 30, 40 and 50 can be inserted between the structures and expanded to an extent that it engages and distracts the structures to permit another surgical procedure to be performed in the space formed by the distraction. In each of these examples the device 30, 40 and 50 would be released and removed after the procedure is completed.

Variations (1) It is understood that variations may be made in the foregoing without departing from the invention and examples of some variations are as follows:
(2) The body members 32, 42, and 52 can take shapes that are different from the examples disclosed above.
(3) The devices 30, 40, 50 and 50' can be inserted in other areas of the anatomy such as, for example, in an intervertebral disc space represented by the references D1-D5 in FIG. 1.
(4) The devices 30, 40, 50 and 50' can be inserted between two vertebrae following a corpectomy in which at least one vertebrae is removed.
(5) The members used to retain the body members 32, 42, and 52 in their collapsed condition can vary.
(6) Any spatial references made above, such as "under", "over", "between", "upper", "lower", "top", "bottom", etc. are for the purpose of illustration only and do not limit the specific orientation or location of the structure described above.

The preceding specific embodiments are illustrative of the practice of the invention. It is to be understood, therefore, that other expedients known to those skilled in the art, or disclosed herein, may be employed without departing from the invention or the scope of the appended claims, as detailed above. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw are equivalent structures.

What is claimed is:

1. A surgical implantation procedure comprising:
applying a sleeve to an expandable member such that the sleeve overlaps a longitudinally-center portion of the expandable member to releasably retain the expandable member in a non-expanded condition with the expandable member having an arcuate collapsed shape inside the sleeve;
thereafter, inserting the expandable member, in the non-expanded condition, between first and second adjacent spinous processes;
expanding the expandable member subsequent to performing the inserting step by introducing fluid into the member via a fill tube associated with the expandable member while the expandable member is disposed within the sleeve;
releasing the sleeve from the inserted expandable member so that the expandable member expands between the first and second adjacent spinous processes;
terminating the step of expanding when the expandable member is in engagement with at least one of the first and second adjacent spinous processes.

2. The procedure of claim 1 wherein the step of expanding comprises inflating the expandable member.

3. The procedure of claim 1 wherein the expandable member is of a generally rectangular shape having two saddles disposed at each end to receive the first and second adjacent spinous processes.

4. The procedure of claim 1 wherein the step of releasing comprises manually removing the sleeve from the expandable member.

5. The procedure of claim 1 wherein the step of releasing comprises allowing the expandable member to break the sleeve during the expansion of the expandable member.

6. The procedure of claim 1 wherein the step of terminating occurs when the spinous processes are stabilized.

7. The procedure of claim 1 wherein the step of expanding causes movement of at least one of the spinous processes, and the step of terminating occurs when the spinous processes are stabilized in a predetermined spatial relationship.

8. The procedure of claim 1 wherein the fluid is taken from a group consisting of air, water, and a curable polymer.

9. The procedure of claim 1 wherein the step of inserting includes inserting the expandable member in the non-expanded condition between first and second spinous processes such that the expandable member in the non-expanded condition is approximately bilaterally centered across the first spinous process.

10. The procedure of claim 5 wherein the step of releasing the sleeve includes breaking the sleeve along at least one perforation extending along the sleeve.

11. A surgical implantation procedure comprising:
inserting a sleeve and an expandable member between first and second adjacent spinous processes, wherein, during the inserting step, the sleeve overlaps a longitudinally-center portion of the expandable member and releasably retains the expandable member in a non-expanded condition with the expandable member having an arcuate collapsed shape inside the sleeve;
expanding the expandable member to an expanded condition subsequent to performing the inserting step by introducing fluid into the member via a fill tube associated with the expandable member while the expandable member is disposed within the sleeve;
releasing the sleeve from the inserted expandable member so that the expandable member expands between the first and second adjacent spinous processes;
terminating the step of expanding when the expandable member is in engagement with at least one of the first and second adjacent spinous processes.

* * * * *